United States Patent [19]

Gokel

[11] Patent Number: 4,474,963

[45] Date of Patent: Oct. 2, 1984

[54] CROWN ETHER COMPOSITIONS WITH SIDEARMS AFFORDING ENHANCED CATION BINDING

[75] Inventor: George W. Gokel, Greenbelt, Md.

[73] Assignee: W. R. Grace & Co., New York, N.Y.

[21] Appl. No.: 440,153

[22] Filed: Nov. 8, 1982

Related U.S. Application Data

[63] Continuation-in-part of Ser. No. 339,529, Jan. 14, 1982, abandoned, which is a continuation-in-part of Ser. No. 203,165, Nov. 3, 1980, abandoned, which is a continuation-in-part of Ser. No. 198,981, Oct. 21, 1980, abandoned.

[51] Int. Cl.$^3$ ............... C07D 215/14; C07D 323/00
[52] U.S. Cl. ............................ 546/178; 546/268; 549/352; 549/353
[58] Field of Search ............... 549/353, 352; 546/268, 546/178

[56] References Cited

U.S. PATENT DOCUMENTS

| | | | |
|---|---|---|---|
| 4,139,539 | 2/1979 | Chamberlin et al. | 549/352 |
| 4,256,859 | 3/1981 | Woo | 549/353 X |
| 4,290,956 | 9/1981 | Sebag et al. | 549/353 |
| 4,297,102 | 10/1981 | Vanlerberghe et al. | 549/353 X |

OTHER PUBLICATIONS

Jungk et al., J. Org. Chem., 48, (1983), pp. 1116–1120.

*Primary Examiner*—Joseph Paul Brust
*Attorney, Agent, or Firm*—Richard P. Plunkett; William W. McDowell, Jr.

[57] ABSTRACT

This invention relates to novel crown ether compositions which have been given the cognomen "lariat ethers". They have been designed with one or more arms bearing neutral donor groups capable of interacting with a complexed metal ion and thereby affording enhanced cation binding compared to simple crown ethers. Evidence of enhanced cation binding has been obtained and the compounds have also shown utility as phase transfer catalysts.

6 Claims, No Drawings

CROWN ETHER COMPOSITIONS WITH SIDEARMS AFFORDING ENHANCED CATION BINDING

BACKGROUND OF THE INVENTION

1. Field of the Invention

This invention relates to new macrocyclic polyether compositions and to complexation of ionic metal compounds therewith.

The novel crown ether compositions of this invention have been given the cognomen "lariat ethers". They have been designed to contain a macrocyclic polyether ring as found in simple crown ethers, but are substituted by a sidearm bearing a neutral Lewis basic donor group such as oxygen or nitrogen. The aforementioned donor group must be at a distance from the macroring such that a metallic cation complexed in the ring will be within bonding (solvating) distance of the donor group. Whereas non-sidearm containing crown ethers whose hole sizes are similar to the cation diameters complex cations by enveloping them in a two-dimensional matrix of donor groups, the sidearm of the lariat ether can reach over and solvate from above, adding a three-dimensional component of solvation to the complex. The concept of roping and tying an animal with a lasso suggests the name "lariat ether" since the ring binds the cation and further stabilization is provided by the sidearm donor group. The name "lariat" comes from the Spanish, la reata = the rope.

2. Description of the Prior Art

The complexation of metallic cations by macrocyclic (crown) polyethers was first demonstrated by Pedersen in 1967 (*J. Amer. Chem. Soc.*, 1967, 87, 7017). Since his original disclosure literally thousands of ether compositions have been prepared. The remarkable structural diversity is apparent from the recent compilation of crown ether structures [G. W. Gokel and S. H. Korzeniowski, *Macrocyclic Polyether Syntheses*, Springer Verlag, Berlin, 1982].

Although crown ethers had been prepared by Luttringhaus and Ziegler (*Justus Liebigs Ann. Chem.*, 1937, 528, 155) about three decades before Pedersen reported his first survey, there was little interest in these molecules. The reason for this is that it was not recognized before Pedersen's reports that the crowns could bind (complex) alkali metal and alkaline earth cations.

The crowns are typically large ring (macrocyclic) compounds characterized by repeating ethyleneoxy ($-CH_2-CH_2-O-$) units. The ability to bind metallic cations in either polar or nonpolar solutions derives from three aspects of the crown's structure. First, there is a hydrophilic or polar cavity which consists of several oxygen atoms. The oxygen electron pairs combine to provide an electron rich coordinating cavity which binds the cation. Second, since the cavity is circular and the metallic cations spherical, there is a complementary relationship between the two. In fact, for any given crown ether, there is a maximum in binding strength when the crown's hole size and the cation diameter are most similar (G. A. Melson, (Ed.) *Coordination Chemistry of Macrocyclic Compounds*, Plenum, N.Y., 1980, p. 145). Third, the exterior of the crown is hydrocarbon-like (lipophilic) and can be solvated by a nonpolar solvent. This configuration of hydrophilic hole and hydrophobic skin provides a solvent gradient within a single molecule. The binding of sodium cation by 15-crown-5 is illustrated in equation 1 below:

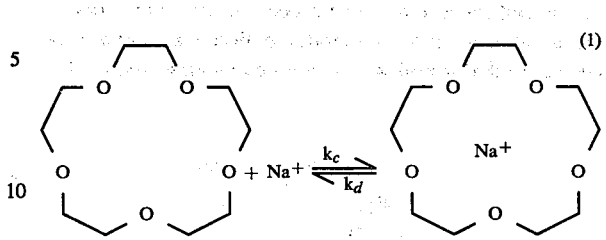

The crown complexes are all highly dynamic (R. M. Izatt and J. J. Christensen, Eds., *Synthetic Multidentate Macrocyclic Compounds*, Academic Press, N.Y. 1978, p. 245). The net binding of a cation is given by the equilibrium stability constant, Ks, which is simply the ratio of complexation ($k_c$) and the decomplexation ($k_d$) rates, i.e., $Ks = k_c/k_d$. The forward or complexation rates are typically near the diffusion-controlled limit, and the magnitudes are about $10^8 M^{-1} sec^{-1}$. Decomplexation rates are also high but must be lower than the complexation rate if Ks is to be greater than unity.

An important point about most crown ether complexes is that the relationship of the cation to the ligand is essentially two-dimensional. That is, the crown wraps about the cation in essentially a plane of donor groups. Since the cation is itself spherical, it seems reasonable to assume that a spherical solvator would be a stronger binder. The cryptands (J. M. Lehn, *Acc. Chem. Res.*, 1978, 11, 49) are very much stronger binders than crowns, and these materials do, in fact, offer the cation a three-dimensional array of binding sites.

A number of compounds having macrorings and sidearms have previously been reported. Notable among these examples are the work of Montanari (*Tetrahedron Letters*, 1979, 5550) and Woo (U.S. Pat. No. 4,256,859). These reports deal with crown compounds bearing sidearms designed to assist in appending the crown ether to a polymer matrix or backbone. Numerous others have reported similar efforts (see, for example, Okahara et al, *J. Org. Chem.*, 1980, 45, 5355). The common feature of all of the compounds described in these reports is that the arm is designed either to enhance the lipophilicity of the crown or to allow for attaching the macroring to a polymer. In no case is any additional binding anticipated from or imputed to these substituted crowns by virtue of sidearm donor interaction.

DETAILED DESCRIPTION OF THE INVENTION

The compounds disclosed herein were all synthesized based on the so-called "lariat ether concept". The key feature of this concept is that there are two elements to the macrocycle. First, there is a cycle of repeating ethyleneoxy units $(CH_2CH_2O)_n$, where n equals 4–8. Appended to the ring is a sidearm bearing a Lewis basic donor group such as oxygen, nitrogen or sulfur. The presence of the Lewis basic group is necessary, but not sufficient, for the lariat ether concept. In our concept, the length of the arm must be such that, when cation complexation by the ring occurs, the donor group can situate itself over the macrocycle and cation and interact with and solvate the cation.

The essential features of a lariat ether are shown schematically in FIG. I below. A macroring of the crown variety is required for primary interaction with the cation. This is represented in the FIGURE by a circle, and the interaction between the crown portion of the lariat ether and the metallic cation is assumed to be similar to that found with other crown ether molecules:

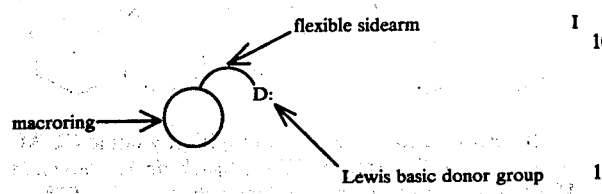

I

The sidearm bearing the Lewis basic donor group (represented herein by -D:) can be a variety of structures but must be capable of allowing the donor group to be positioned over the ring-bound cation and interact with it. From the crystal structures of complexes between a variety of crown ethers and cations, this distance must be approximately 1.8–3.3 angstroms (A) and will obviously be both donor group and cation dependent.

It is known, for example, that the interaction between nitrogen atom donors and such transition metals as nickel (II) involves a bonding distance from donor to metallic cation of about 2.0 A. Furthermore, most of the known potassium-to-oxygen interactions involve distances of about 2.8 A. Although these numbers are not precise, they serve to define the range involved in this concept. Clearly, if the donor group were present but held at a distance from the ring of 0.5 A., it would be unacceptable for secondary binding of the ring-bound cation. On the other hand, if the donor were held at a distance of 5 A. from the ring with no possibility of folding back on itself to become near the ring, it would simply be too remote to be useful.

The concept which distinguishes the compounds described herein from those compounds which may appear superficially similar, is that all contain a sidearm bearing Lewis basic donor groups. Although some of the compounds described here may be appended to a polymer backbone in much the same way as suggested for other compounds, this is not the major implication of these sidearms.

This point can be made quite clearly by comparing two similar compounds. t-Butoxymethyl-18-crown-6 is prepared by both Montanari and Woo (see above). In both of these the sidearm is a precursor to the hydroxymethyl group by removal of the t-butyl residue. The hydroxymethyl residue is then available for further substitution and reaction. We have prepared the related n-butoxymethyl-15-crown-5 in order to demonstrate the difference between these concepts. Note that chemically the n-butyl group is much more difficult to remove than is the t-butyl group. It was synthesized not in the hope that it could be removed, but so that its binding could be compared with a compound identical except for the presence of a Lewis basic donor group in the side arm. The two compounds compared are shown below in FIGS. II and III:

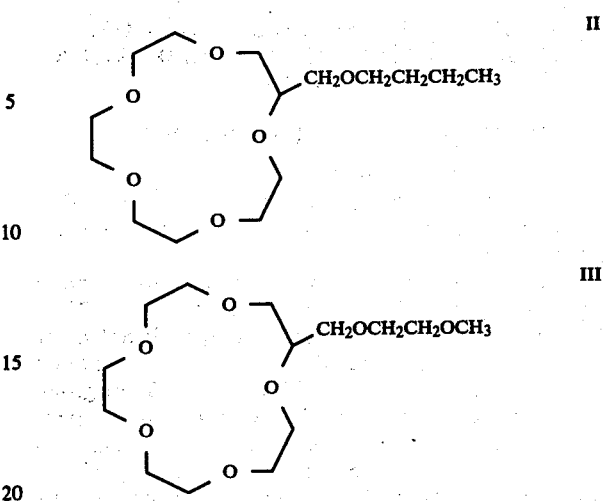

Note that in each case there are six non-hydrogen atoms in the sidechain. In one case (III) there is a donor atom present in the sidechain at a distance from the macroring which should be useful for secondary binding, and in the other case (II) no such heteroatom is present. In all of the compounds claimed herein a donor group is present in the sidechain, and each substance conforms to the general structure (I), shown above, in which the circle represents a macrocyclic polyether ring of 12–21 members and D represents a Lewis basic donor group.

In all of the compounds herein the point of attachment of the sidearm to the macroring is carbon. Thus, the general structure shown above as I can be refined into a more detailed structure as follows:

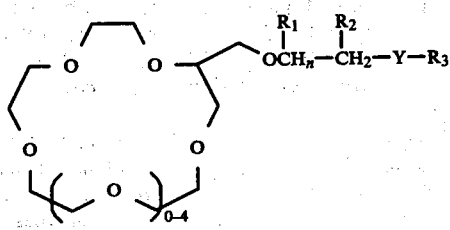

The essential structural feature of the claimed compounds is the presence of a heteroatom $Y=N$ or $O$ which is two carbons removed from an oxymethylene group attached to the crown. The substituent $R_3$, per se, on Y should be such that a hydroxyl (—OH), amino (—$NH_2$) or carboxyl (—COOH) group does not result. This is because hydrogen bonding between any of these three functional groups and a protic solvent would tend to orient the sidearm with respect to the solvent and not with respect to the ring. As such, the sidearm would not be correctly disposed to align itself for secondary solvation of the ring-bound cation.

The value of n is equal to 0 or 1. When $n=1$, $R_1$ and $R_2$ are independently selected from H, alkyl, alkenyl and substituted (as defined below) or unsubstituted aromatic rings selected from the group consisting of carbocyclic aryl, carbocyclic aralkyl, pyridyl and quinolyl. When $n=0$, $R_1$ and $R_2$ form part of a substituted (as defined below) or unsubstituted aromatic ring selected from the group consisting of carbocyclic aryl, carbocyclic aralkyl, pyridyl or quinolyl. $R_3$ is alkyl, (alkoxy)$_q$ alkyl or aralkoxy(alkoxy)$_q$alkyl, wherein q is 1-4, substituted (as defined below) or unsubstituted aromatic ring selected from the group consisting of carbocyclic aryl, carbocyclic aralkyl or may be part of a quinoline ring also encompassing $R_1$, $R_2$ and Y. The substituents on the aromatic ring of $R_1$, $R_2$ and $R_3$, subject, however, to the above mentioned restriction on $R_3$, include, but are not limited to, halogen, alkyl, alkoxy, $NH_2$, alkyl—NH—, dialkyl—N—, cyano, nitro, —O—CO—R, —O—CO—Ar, —COOR, —COOAr, NH—COR, —NH—COAr, —CO—NHR, —CONHAr, —CO—H, —CO—R, —CO—Ar, hydroxyalkyl, mercaptoalkyl, alkylene, —SR, —SAr, —S—CO—R, —S—CO—Ar, —O—R, —O—Ar, —S—CS—R, —S—CS—Ar, —O—CS—R, —O—CS—Ar, alkoxyalkyl, thioalkoxyalkyl and combinations thereof, said R being an alkyl group of 1-14 12 carbons and said Ar being a carbocyclic aryl group containing up to 15 carbons and said substituents being present up to the maximum number of free positions on the ring. Due to their nature and/or position on the aromatic ring, these substituents are designed not to be involved in the binding nor is the carbon content of R or Ar crucial and are, therefore, not a limiting feature of the invention.

Because the binding process is a complex one, it may not always be possible to directly verify the participation of the arm in the binding. What verification there is, however, must obviously come from binding studies. Binding data can be obtained in a variety of ways, two of which are described here.

a. METHOD A—Extraction Constants

It is well known from the work of Pedersen and Frensdorff (*Angew. Chem. Int. Ed. Engl.*, 1972, 11, 46) that the association between a metallic cation and an anion can be assessed by the ability of a crown to transport M+ picrate[31] (m=Na, K) from aqueous to organic media. Sodium and potassium picrate are insoluble in such organic solvents as $CH_2Cl_2$ but are readily soluble in water. When a solution of either sodium or potassium picrate is shaken with a solution of crown in dichloromethane, the crown complexes the cation and extracts it into the organic phase. The yellow picrate anion accompanies the crown-cation complex rendering the organic phase yellow. Clorimetric determination (by ultraviolet spectroscopy) allows a comparison to be made of the complexing ability of various crowns.

The so-called "extraction constants" are given as the percentage of available salt (in the aqueous phase) extracted into the organic phase. The extraction constant for 15-crown-5 is shown in TABLE I along with several others. The former is used as a standard for comparison of values.

b. METHOD B—Equilibrium Binding or Stability Constants, Ks.

The ability of a ligand to bind a cation can also be expressed as the stability of the resulting complex. This is an equilibrium relationship and is measured in a homogeneous solution. It is important to note that the stability constants are determined in very polar solvents like 90% methanol whereas the extraction constants reflect the stability of the ligand-cation complex in a nonpolar solution like dichloromethane. It has been found that the equilibrium constant for the reaction between 15-crown-5 and sodium cation is more than 25 times higher in methanol than it is in water although both are quite polar solvents.

The binding or stability constants reported here were measured electrochemically. The conductivity of a solution of salt in the chosen solvent was determined relative to a standard calomel electrode. Ligand was then added and, after allowing time for equilibration, the conductivity was measured using an ion selective electrode as before. The difference in conductivity is proportional to the binding strength and can be related mathematically to the equilibrium constant, given in equation (1):

$$\text{ligand} + \text{salt} \underset{}{\overset{K_s}{\rightleftharpoons}} \text{complex}$$

The equilibrium binding constants were, of necessity, measured in polar solvents which could dissolve the salt in the absence of the ligand. As a result the equilibrium constants, Ks, and the extraction constants (see above) are not directly comparable although they give similar information.

ANALYSIS OF BINDING DATA

Note that all of the compounds which seem to give enhanced binding (see TABLE I) have a heteroatom in a position to afford secondary solvation to a ring-bound cation:

TABLE I

| | | Method A Extraction Constant | Method B Ks for Na+ in | |
|---|---|---|---|---|
| | Sidearm attached to 15-crown-5 | Na+, $H_2O$/ $CH_2Cl_2$ | 90% Methanol | Pure Methanol |
| 1.* | H | 7.6% | 932 | 1862 |
| 2.* | $CH_2OCH_2$ | 5.1% | 550 | 1071 |
| 3.* | $CH_2OCH_2CH=CH_2$ | 7.0% | 540 | nd |
| 4.* | $CH_2OCH_2CH_2CH_2CH_3$ | 10.3% | nd | nd |
| 5.* | $CH_2OC(CH_3)_3$ | 7.2% | 645 | nd |
| 6.* | $CH_2$—O—CO—$CH_3$ | 3.6% | 229 | nd |
| 7. | $CH_2OCH_2CH_2OCH_3$ | 18.0% | 676 | 1122 |
| 8. | $CH_2OCH_2CH_2OCH_2CH_2CH_3$ | 11.2% | 737 | 1230 |
| 9. | $CH_2O(CH_2CH_2O)_2CH_3$ | 15.7% | 871 | 1350 |
| 10.* | $CH_2O(CH_2CH_2O)_2H$ | 15.3% | 631 | nd |
| 11. | $CH_2O(CH_2CH_2O)_3CH_3$ | 19.8% | 707 | 1230 |
| 12.* | $CH_2OPh$ | 4.0% | 323 | nd |
| 13.* | $CH_2OCH_2Ph$ | 7.9% | 550 | nd |

TABLE I-continued
Extraction and Stability Constants for Lariat Ethers

| Sidearm attached to 15-crown-5 | Method A Extraction Constant Na+, H2O/CH2Cl2 | Method B Ks for Na+ in 90% Methanol | Method B Ks for Na+ in Pure Methanol |
|---|---|---|---|
| 14. (CH2O, CH3O on benzene) | 15.7% | 933 | 1738 |
| 15.* (CH2O, OCH3 on benzene) | nd | 371 | 724 |
| 16.* (CH2O—benzene—OCH3, para) | 6.4% | 363 | nd |
| 17.* (CH2O-naphthalene) | nd | 550 | nd |
| 18.* (CH2O-quinoline) | nd | 2455 | nd |
| 19. (CH2O, CH3O on benzene with propyl) | 24.3% | 871 | nd |
| 20. (CH2O, CH3O on benzene with allyl) | 15.7% | 724 | nd |
| 21. (CH2O, CH3O on benzene with CH2CH(OH)CH3) | 14.2% | 851 | nd |

*indicates compounds which are outside the scope of the invention and are shown only for comparative purposes.
(nd) These values have not been determined, and no data are available on them, to our knowledge, from any source.

Two especially interesting comparisons can be made in the compounds having carbon as a point of attachment for the sidearm. Note that the extraction constants for phenoxymethyl-15-crown-5 (IV or cpd. 12 in TABLE I):

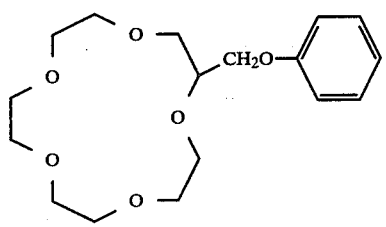

IV and ortho-methoxyphenoxymethyl-15-crown-5 (V or cpd. 14 in TABLE I):

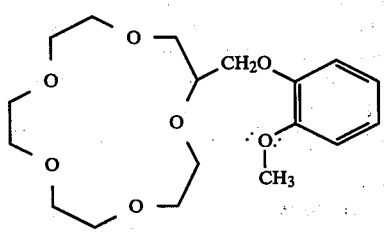

are quite different. The extraction constant for the former which does not have a sidearm donor atom in a position appropriate for secondary binding has an extraction constant of 4.0%, even lower than the percent of sodium picrate extracted by the unsubstituted parent, 15-crown-5. In the ortho-methoxy compound donation (solvation) by the methoxy oxygen is possible and the extraction constant (15.7%) reflects this. Simply moving the methoxy group from the ortho to the para position where it is no longer sterically accessible to the ring-bound cation (cpd. 16 in TABLE I) eliminates this secondary interaction with a resulting decline in the extraction constant (to 6.4%). These notions are illustrated schematically in FIG. VI wherein dotted lines indicate donor interactions and dashed lines indicate stereochemical relationships:

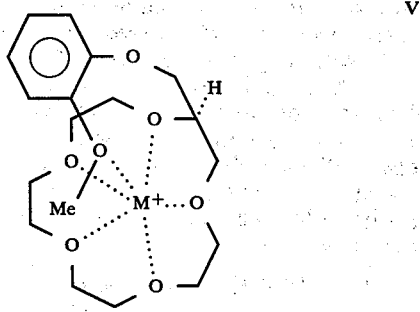

That the "enhanced cation binding" design criterion is met for many of these compounds is illustrated by the data recorded in TABLE I. As noted above, two kinds of binding "constants" are presented therein. The extraction constants are determined by partitioning sodium picrate between dichloromethane and water in the presence of a crown. The percent of salt extracted in the presence of crown relative to the amount available is recorded as the "extraction constant". In the absence of the ligand no salt dissolves in dichloromethane. The "binding or stability constants, Ks" are equilibrium constants for the homogeneous reaction:

The two kinds of constants are not directly comparable since they are determined differently, involve heterogeneous vs. homogeneous media and involve different salts. Nevertheless, both "constants" give similar information and comparisions can be made between similar compounds in the similar media. The compound numbers used below refer to entries in TABLE I.

Better information can be obtained by a comparison of extraction constants since the association phenomenon is more pronounced in the less polar solvent, dichloromethane. Note that addition of any short, non-lipophilic, non-binding sidearm to the 15-crown-5 moiety reduces the binding relative to the parent (cpd. 1). Thus, addition of the methoxymethyl sidearm (cpd. 2) causes a drop in extraction constant compared to 15-crown-5 (cpd. 1). Thus, comparisons of binding strength in this group should be made with cpd. 2 rather than cpd. 1.

Some conclusions can be drawn immediately. First, addition of a simple sidearm reduces binding in general (see also Ks values) and increasing the length and lipophilicity of the sidearm increases binding relative to short sidearms. Thus, the methoxymethyl sidechain (cpd. 2) leads to reduced binding relative to 15-crown-5 (cpd. 1), but binding is not reduced as much for the t-butoxymethyl crown (cpd. 5) whose binding constant is nearly the same as for 15-crown-5. The normal butyl group in Cpd. 4 affords even more favorable binding than does the tertiary butyl group as expected for their relative lipophilicities. Both compounds 4 and 7 have six non-hydrogen atoms in a straight sidechain. The n-butoxy compound (cpd. 4) does not have an oxygen in a position sterically accessible to the ring-bound cation, but the remote oxygen in the 2-methoxyethoxy crown (cpd.7) is correctly disposed for such binding. The extraction constant in the latter case is considerably higher than is the former's. Another comparison of this type is found in the extraction constants for ortho-methoxyphenoxymethyl-15-crown-5 (cpd. 14) and its para-isomer (cpd. 16) as discussed supra. The ortho-methoxy group is suitable placed so that the oxygen can serve as a donor, but the para-oxygen is too remote. The same binding enhancement is obvious in the ring-substituted relative (cpd. 19) of cpd. 14.

Compounds 17 and 18 constitute another interesting comparison. The two compounds differ only by the presence of a nitrogen in the second aromatic ring. Note that the two-carbon separation between the first (inactive) heteroatom and the second one are realized in this case as well. Although extraction constant data have not been determined for this pair, the binding constants show the dramatic difference made by this single, properly placed heteroatom. Equilibrium binding constants for these two species are, respectively, 550 (for cpd. 17) and 2,455 (cpd. 18).

COMPARISON OF LARIAT ETHERS TO PRIOR ART COMPOUNDS

Some of the compounds claimed herein bear a superficial resemblance to a few of the compounds taught in U.S. Pat. No. 4,256,859. These compounds of U.S. Pat. No. 4,256,859 are monocyclic crown ethers which have (—CH$_2$—CH$_2$—O—)$_n$ sidearms all of which are terminated in a hydroxyl group remote from the macrocyclic ring. However, there is no specific example of the preparation of these compounds, and no evidence is presented relating to their binding ability.

Two distinguishing aspects of our invention from the polyethylene glycol-derived compounds taught in U.S. Pat. No. 4,256,859 are the mode of synthesis and the properties of the resulting products. First, the mode of synthesis suggested is to treat a hydroxymethyl crown with base to form an alkoxide ion which will oligomerize ethylene oxide. This type of reaction is well known, and the result of such a reaction is almost invariably the formation of oligomeric mixtures of the type crown —CH$_2$—O—(CH$_2$CH$_2$O)$_n$—H. Although specific chain lengths of n=1-5 are taught, there is no evidence that these individual species could be obtained in a pure state, even with difficulty, since their physical properties would be so similar. These sidechains are considered only in the terms of the claims as mechanical links, and no recognition is made of the disadvantages of hydroxyl termination or variation in chain length with respect to cation binding.

The binding power of a number of lariat ethers having both carbon-pivots as in the present case and nitrogen-pivots has been examined, and it has been found that, after a certain relatively small number of ethyleneoxy units are incorporated, the cation binding strength levels off and then declines. Thus, although the first few oxygens may be capable of serving as Lewis basic donor groups to the ring-bound cation, the outer oxygens in the chain serve as hydrogen bond acceptors from solvents like methanol or water. Hence, the longer the chain, the greater the hydrogen bonding, and the less available the sidechain is for secondary solvation of the ring-bound cation. Any potential binding ability imparted to these molecules by these sidechains would certainly diminish for the longer chain species. In such a case, the binding properties claimed in our own compounds would not be inherent in the compounds taught in U.S. Pat. No. 4,256,859, or at least the property would be considerably attenuated therein.

A second aspect of the problem has to do with the presence of the hydroxyl terminus in the polyethyleneoxy compounds of U.S. Pat. No. 4,256,859. Without the hydroxyl group which could be used as a nucleophile for attaching the tethered macroring to a resin, the object of the patent would be unfulfilled. The presence of the hydroxyl group in the compounds of U.S. Pat. No. 4,256,859 compared to those herein (which are all methyl or benzyl terminated) makes major differences in the properties. First, the compounds herein could not be utilized in the way suggested in U.S. Pat. No. 4,256,859 without removal of the methyl group for cation binding. More importantly, however, the great disadvantage of the terminal hydroxyl for cation binding is that now there is a hydrogen bond *donor* in the system as well as hydrogen bond acceptors. The terminal hydroxyl group should be heavily solvated in protic solvents, and the solvation around it could easily prohibit involvement of the sidechain according to the lariat ether concept.

One of the applications suggested in U.S. Pat. No. 4,256,859 for these compounds is as phase transfer catalysts. The phase transfer process (see W. P. Weber and G. W. Gokel, *Phase Transfer Catalysis in Organic Synthesis*, Springer Verlag, Berlin, 1977) involves transport of a chemical species across a phase boundary, nearly always a water/nonpolar organic solvent interface. A model for this process is found in the so-called "extraction constants" discussed above and shown in TABLE I as "Method A". In this technique, an aqueous reservoir of a colored salt is exposed to a complexing agent which binds it and draws it into the organic phase. The effectiveness of this process is determined by the solvents and salts involved, and so a non-normalized percentage scale is used. The extraction constant percentage reflects the percent of total salt (usually a large excess) present in the aqueous phase which is extracted into the nonpolar solution. In comparisons of these values, then one should refer all values to the range of numbers actually observed for the particular experiment in question rather than to some arbitrary scale such as 0-100.

An examination of the compounds shown in TABLE I shows that the most effective extractor is compound 19, which extracts 24.3% of the available salt into dichloromethane. The poorest extractor shown (a compound which is not claimed but included only for comparative purposes) is compound 6, an ester which extracts only 3.6% of the available salt into dichloromethane. The range of values here is thus only 21 percentage points from best to worst.

Because of the lack of flexibility in the carbon-pivot lariat ethers, it has been found that the homogeneous binding constants are far less sensitive measures of binding differences than are the extraction constants. This probably explains why extraction constants are so much more widely used in the literature than are the binding constants. The main focus, therefore, is on these extraction constants because they are believed to be more sensitive and because they better represent the phase transfer process.

Although no procedure was given in U.S. Pat. No. 4,256,859, for its preparation, a three-ethyleneoxy unit crown of the type taught therein was synthesized by the procedure of Example 18 of the instant invention. This compound (cpd. 10 in TABLE I) has an extraction constant of 15.3%. Compound 11 (a lariat ether of the instant invention) has the same structure except that it is methyl-terminated rather than hydroxyl-terminated. The extraction constant for cpd. 11 is 19.8%. As discussed above, a compressed scale of values from approximately 4%-24% is used herein; so the difference of 4.5 percentage points actually reflects a difference of over 20% in binding capability on a normalized scale of 0 to 100. Compound 10 does not have a long enough chain to be one of the poorest binders of the compounds disclosed in U.S. Pat. No. 4,256,859 but rather should be one of the best of that disclosure. Even so, it is notably poorer in binding than the compounds claimed in the instant invention.

SPECIFIC EXEMPLIFICATION OF THE INVENTION

The following examples are set forth to illustrate, but expressly not limit, the instant invention. Unless otherwise noted, all parts and percentages are by weight:

EXAMPLE 1

3-Benzyloxy-2-hydroxypropyl Chloride Preparation

A 1,000 mL, 3-necked flask equipped with a mechanical stirrer, condenser, thermometer and 500 mL addition funnel was charged with benzyl alcohol (324 g, 3.0 mol) and 5% BF$_3$-etherate in ether (10 mL). This mixture was stirred and heated to 80° C. Epichlorohydrin (278 g, 3.0 mol) was added dropwise over 6 hours, and the reaction mixture was stirred an additional 24 hours at 80° C. The crude product was distilled from NaHCO$_3$ (1 g) using a 25 cm Vigreux column. The fractions boiling from 95° C. (0.05 mm) to 120° C. (0.03 mm) were collected and combined to yield 353 g (58%) of pure 3-benzyloxy-2-hydroxypropyl chloride.

3-Benzyloxy-1,2-epoxypropane Preparation

A 2,000 mL, 3-necked flask equipped with a mechanical stirrer and thermometer was charged with 3-benzyloxy-2-hydroxypropyl chloride (353 g, 1.76 mol) and dichloromethane (1,000 mL). This mixture was stirred and cooled in an ice bath to ca. 5° C. Aqueous 50% NaOH (176 g) was added in portions while the temperature was kept under 30° C. After addition was complete, the reaction mixture was stirred 4 hours at 25° C. Water (1,000 mL) was added to dissolve the salts. The organic phase was separated from the aqueous phase, washed with ice water (3×500 mL), dried and reduced in vacuo to yield 263 g (92%) of pure 3-benzyloxy-1,2-epoxypropane.

3-Benzyloxy-1,2-propanediol Preparation

3-Benzyloxy-1,2-epoxypropane (263 g, 1.60 mol), water (1,300 mL) and 70% perchloric acid (1.5 mL) were placed in a 2.0 L 3-necked flask equipped with condenser and thermometer. The mixture was heated to 80° for 18 hours. After heating and stirring for 18 hours at 80° the reaction mixture was neutralized with 5% sodium bicarbonate solution. The water was removed by rotary evaporation. Final removal of residual water was accomplished by azeotropic distillation using 300 mL of benzene. After evaporation of the benzene the product was distilled to yield 264 g (90%) of 3-benzyloxy-1,2-propanediol: bp 127°–136° C. (0.04 mm).

Tetraethylene Glycol Dimesylate Preparation

A 5,000 mL, 3-necked flask equipped with a mechanical stirrer, thermometer and 500 mL addition funnel was charged with tetraethylene glycol (388 g, 2.0 mol) dichloromethane (1,500 mL) and triethylamine (445 g, 4.40 mol). The mixture was stirred and cooled to ca. 5° C., and methanesulfonyl chloride (470 g, 4.1 mol) was added dropwise over 3 hours. The reaction mixture was stirred an additional 3 hours while warming to 25° C., then water (1,000 mL) was added and the phases were separated. The organic layer was washed with ice-cold 6N HCl (2×1,000 mL) and then washed with 5% Na$_2$CO$_3$, saturated aqueous NaCl, dried, filtered and evaporated in vacuo to yield 627 g (90%) of tetraethylene glycol dimesylate, i.e.,

CH$_3$SO$_2$—O—(CH$_2$CH$_2$O)$_4$SO$_2$CH$_3$ as an analytically pure, amber oil: NMR (CDCl$_3$), 3.0 (s, 6H), 3.5–4.0 (m, 12H), 4.3–4.5 (m, 4H); IR 3030, 2940–2880 (s), 1450, 1350 (s), 1170 (s), 1140 (s), 1110 (s), 1020 (s), 970 (s), 920 (s), 800 (s), 730 cm$^{-1}$. Anal. Calcd for C$_{10}$H$_{22}$O$_9$S$_2$: C, 34.28; H, 6.33; S, 18.30. Found: C, 33.98, H, 6.50; S, 18.00.

Benzyloxymethyl-15-crown-5 Preparation

A 5,000 mL, 3-necked flask equipped with a mechanical stirrer, reflux condenser and 500 mL addition funnel was charged with sodium hydride (52.8 g, 1.10 mol). The mineral oil in the sodium hydride was removed by washing with hexanes (4×250 mL) and syringing the spent solvent from the flask. THF (2,500 mL) was added and the resulting mixture stirred and heated to reflux. A mixture of 3-benzyloxy-1,2-propanediol (91.1 g, 0.50 mol) and tetraethylene glycol dimesylate (175 g, 0.50 mol) was diluted with THF to a volume of 500 mL. The mixture was added to the NaH suspension over several hours and the reaction mixture was stirred an additional 14 hours at reflux. The THF was distilled from the reaction vessel leaving behind a slurry of crude crown and salts. Water (1,500 mL) was added to dissolve the salts, and the resulting solution and acidified with 6N HCl to pH=2. The aqueous mixture was extracted with dichloromethane (2×1,000 mL), then the organic solution was dried and reduced in vacuo to leave 164 g of crude, oily crown. The residue was chromatographed on alumina (7×25 cm) with 0–10% 2-propanol/petroleum ether (bp 35°–60° C.) to yield 106 g (62%) of benzyloxymethyl-15-crown-5, i.e.,

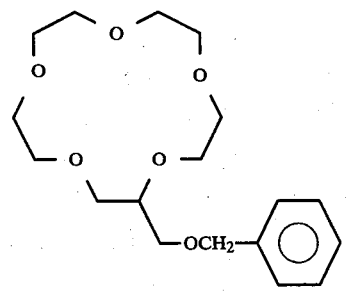

in a form sufficiently pure for the preparation of hydroxymethyl-15-crown-5. An analytical sample was prepared by chromatography on alumina (0–2% 2-propanol/ligroine): NMR (CDCl$_3$), 3.6 (bs, 21H), 4.5 (s, 2H), 7.25 (s, 5H); IR 3060, 3030, 2980–2800 (s), 1450 (s), 1350, 1300, 1250, 1200, 1150–1060 (s), 970, 940, 845, 735 (s), 700 (s) cm$^{-1}$. Anal. Calcd for C$_{18}$H$_{28}$O$_6$: C, 63.51; H, 8.29. Found C, 63.25; H, 8.58. Extraction constants (CH$_2$Cl$_2$/H$_2$O) were found to be: Na$^+$, 7.9%; K$^+$, 5.8%.

EXAMPLE 2

Hydroxymethyl-15-crown-5 Preparation

A 500 mL Paar bottle was charged with benzyloxymethyl-15-crown-5 (53 g, 0.156 mol), absolute ethanol (250 mL) and 10% Pd/C catalyst (4 g). The reaction mixture was shaken 12 hours at 25° C. under a hydrogen pressure of 60 psi and then filtered twice through a bed of alumina in a glass-frit funnel. The combined solutions were reduced in vacuo to leave 73.5 g of crude hydroxymethyl-15-crown-5. The residue was chromatographed on alumina (7×25 cm) with 0–10% 2-propanol/ligroine to yield 39.0 g (50%) of analytically pure hydroxymethyl-15-crown-5, i.e.,

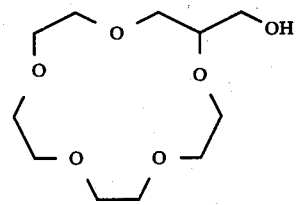

NMR (CDCl$_3$): 2,6 (bs, 1H); 3.63 (bs 21H); IR 3500–3100 (s), 3000–2800 (s), 1450, 1350, 1290, 1250, 1150–1020 (s), 980, 940, 840 cm$^{-1}$. Anal. Calcd for C$_{11}$H$_{22}$O$_6$: C, 52.78; H, 8.86. Found: C, 53.06; H, 9.14. Extraction constants (CH$_2$Cl$_2$/H$_2$O) were found to be: Na$^+$, 2.7; K$^+$, 4.4; log K$_s$(H$_2$O) was found to be 0.79.

EXAMPLE 3

3-Allyloxy-1,2-propanediol Preparation

A 5,000 mL, 3-necked flask fitted with a mechanical stirrer, thermometer and 500 mL addition funnel was charged with water (2,000 mL) and 70% aqueous HClO$_4$ (2.0 mL), then heated to 80° C. Allyl glycidyl ether (500 g, 4.38 mol) was added in one portion and the reaction mixture stirred for 12 hours. The mixture was neutralized by addition of 5% aqueous $Na_2CO_3$ to pH=8. The water was evaporated in vacuo to leave 550 g of crude product, which was distilled to yield 498 g (86%) of pure 3-allyloxy-1,2-propanediol: bp 76°-83° C. (0.4 mm).

EXAMPLE 4

Tetraethylene Glycol Ditosylate Preparation

A 3,000 mL, 3-necked, round bottomed flask was equipped with a mechanical stirrer, a thermometer and a 250 mL addition funnel, with a drying tube atop. Toluenesulfonyl chloride (419 g, 2.2 mol), pyridine (237 g, 3 mol) and dichloromethane (750 mL) were placed in the flask. This mixture was stirred mechanically and cooled to approximately 5° C. in an ice-water bath. Tetraethylene glycol (194.2 g, 1 mol) was added over a 1 hour period, after which time the addition funnel was replaced by a reflux condenser. The ice-bath was removed. The reaction mixture was heated to 36°-38° C. When the mixture cooled to below 30° C., 1,000 mL of water was added to the salts. The phases were separated and the organic layer washed with ice-cold 6N HCl (2×200 mL), water (200 mL), brine (200 mL) and finally dried over sodium sulfate. The crude ditosylate was used directly in other preparations.

Allyloxymethyl-15-crown-5 Preparation

A 5,000 mL, 3-necked flask equipped with a mechanical stirrer, efficient reflux condenser and 500 mL addition funnel was charged with sodium hydride (47.3 g, 0.98 mol). The mineral oil in the sodium hydride was removed by washing with hexanes (4×200 mL) and syringing the spent solvent from the flask. THF (2,000 mL) was added and the resulting mixture stirred and heated to reflux. A mixture of 3-allyloxy-1,2-propanediol (54.1 g, 0.41 mol) and tetraethylene glycol ditosylate (206 g, 0.41 mol) was diluted with THF to a volume of 500 mL. The mixture was added to the NaH suspension over several hours and the reaction mixture was stirred an additional 14 hours at reflux. The precipitated salts were removed by vacuum filtration, and the THF was evaporated in vacuo to leave 96 g of crude oily crown. The residue was extracted exhaustively with hexanes to afford 66 g of a pale yellow oil, which upon which fractional distillation gave 40 g (34%) of allyloxymethyl-15crown-5, i.e.,

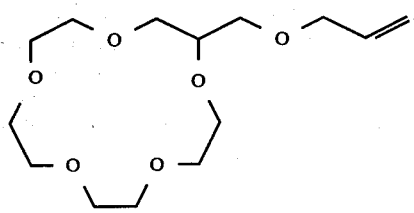

bp 134°-140° C. (0.05 mm); NMR (CCl4), 3.53 (bs, 21H), 3.8-4.0 (d, 2H), 4.9-5.3 (bm, 2H), 5.5-6.1 (bm, 1H); IR 3080, 2860 (s), 1450, 1350, 1295, 1250, 1130 (s), 980, 930 cm$^{-1}$. Anal. Calcd for $C_{14}H_{26}O_6$: C, 57.91; H, 9.03. Found: C, 57.63; H, 9.30.

EXAMPLE 5

(2-Hydroxypropoxy)methyl-15-crown-5 Preparation

Mercuric acetate (3.19 g, 10.0 mol) was placed in a 50 mL flask equipped with a condenser and thermometer. Water (10 mL) and THF (8 mL) were added. Allyoxymethyl 15-crown-5 (1.45 g) was added at once and rinsed in with 2 mL of THF. A slight rise in temperature from 26° to 30° C. was noted. The reaction mixture was stirred for ½ hour and then 3N NaOH (2 mL) was added, followed by 1M $NaBH_4$/10% NaOH (7 mL). A temperature rise to 40° C. was observed, and the reaction mixture was stirred for an additional 0.5 hour. The reaction mixture was filtered into a 100 mL flask and the THF was evaporated. The product was extracted with dichloromethane (5×25 mL), dried and filtered through celite. The solution was evaporated in vacuo to yield 2-hydroxypropoxymethyl-15-crown-5, i.e.,

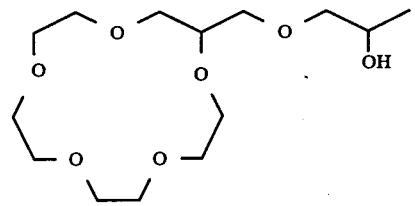

(1.45 g, 94%). NMR 1.1-1.2 (d, 3H), 2.9 (bs, 1H), 3.63 (bs, 24H); IR 3400-3200 (s), 2960-2840 (s), 1450, 1300, 1250, 1150-1050 (s), 1030, 950, 850. Anal. Calcd for $C_{14}H_{28}O_7$; C, 54.53; H, 9.15. Found: C, 54.27: H, 9.42. This compound exhibited a binding constant in aqueous solution (log Ks) of 2.03.

EXAMPLE 6

4-Allyl-2-Methoxyphenyl Glycidyl Ether Preparation

A 2,000 mL, 3-necked, round-bottom flask was equipped with a mechanical stirrer, a 250 mL pressure equalizing addition funnel and a reflux condenser. The addition funnel served as the $N_2$ inlet and the reflux condenser served as the $N_2$ outlet. The flask was purged with a vigorous stream of $N_2$ for 10 min. prior to its use. The flask was charged with epichlorohydrin (740 g, 8.0 mol) and eugenol (328 g, 2.0 mol). These were heated to ca. 80° using a heating mantle while stirring at a moderate rate (ca. 500 rpm). The 50% NaOH (168 g, 2.0 mol) was placed in the addition funnel and was added dropwise to the reaction flask over a 3 hour period. The mixture was allowed to cool and was filtered through a Buchner funnel. The epichlorohydrin was removed by rotary evaporation. The residue was taken up in $CH_2Cl_2$(800 mL) and was washed with 10% NaOH (100 mL) brine and dried ($Na_2SO_4$). The crude product was vacuum distilled through a 10 cm Vigreux column to yield 4-allyl-2-methoxyphenyl glycidyl ether, i.e.,

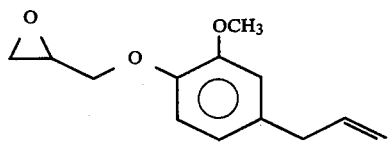

3-(4-Allyl-2-methoxyphenoxy)-1,2-propanediol Preparation

A 3,000 mL, 3-necked, round-bottom flask was equipped with a mechanical stirrer, a reflux condenser and a 250 mL addition funnel. The flask was charged with $H_2O$ (1,500 mL) and 70% $HClO_4$ (1 mL) and heated to ca. 80° C. while stirring vigorously (ca. 750 rpm). 4-Allyl-2-methoxyphenyl glycidyl ether was placed in the addition funnel and was added dropwise to the reaction mixture over a 4-5 hour period. The reaction mixture was stirred for 48 hours at ca. 80° C. The mixture was then allowed to cool and was neutralized with 5% Na$_2$CO$_3$. The phases were separated and the aqueous phase extracted with CH$_2$Cl$_2$ (1,500 mL). The CH$_2$Cl$_2$ and H$_2$ were removed from the 3-(4-allyl-2-methoxyphenoxy)-1,2-propanediol, i.e.,

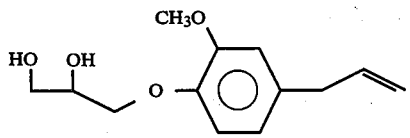

by evaporation in vacuo to yield a pale amber oil (355 g, 97%) which crystallized on standing; mp 77°-79° C. (recrystallized from benzend).

(4-Allyl-2-methoxyphenoxy)methyl-15crown-5 Preparation

A 5,000 mL, 3-necked, round-bottom flask was equipped with a mechanical stirrer, a 500 mL pressure equalizing addition funnel and reflux condenser. A N$_2$ inlet was attached to the top of the addition funnel, and the N$_2$ was vented through the reflux condenser. The assembly was purged with a vigorous stream of N$_2$ prior to its use. The flask was then charged with NaH (50.4 g, 1.05 mol) which was then washed with hexanes (3×200 mL) to remove most of the paraffin oil. The NaH was then suspended in THF (2.5 L, freshly distilled from LAH) with vigorous stirring (ca. 750 rpm). The NaH/THF suspension was heated to a gentle reflux and the N$_2$ purge was slowed. The 3-(4-allyl-2-methoxyphenoxy)-1,2-propanediol 119 g, 0.50 mol) and tetraethylene glycol ditosylate (251 g, 0.50 mol) were dissolved in THF (200 mL) and the resulting solution was placed in the addition funnel. It was then added dropwise to the flask over a 5 hour period so as to maintain a steady evolution of H$_2$. The mixture was allowed to stir at reflux for an additional 24 hours. It was then allowed to cool and was filtered through a large Buchner funnel to remove the salts. The THF was removed by evaporation in vacuo. This crude amber oil was column chromatographed on alumina (7×60 cm column; 500 g alumina). Eluents petroleum ether (bp 35°-60° C., 1,500 mL), 3% 2-propanol/petroleum ether (v/v, 2,000 mL). This yield pure (4-allyl-2-methoxyphenoxy)methyl- 15 -crown-5, i.e.,

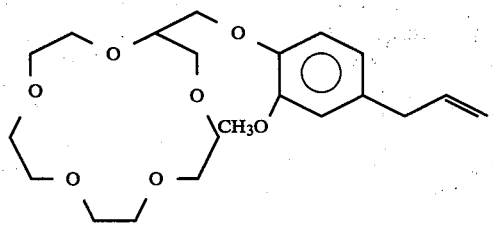

as a yellow oil (124 g, 63%). NMR (CDCl$_3$) 3.2-3.4 (bd, 2H), 3.5-4.2 (m, 24H), 4.9-5.3 (bd, 2H), 5.6-6.4 (m, 1H), 6.6-7.0 (m, 3H; IR (neat) 3060, 3000, 2865, 1635, 1600, 1585, 1510, 1465, 1450, 1420, 1345, 1260, 1230, 1130 (s), 990, 930, 850, 800, 745 cm$^{-1}$. Anal. Calcd for C$_{21}$H$_{32}$O$_7$: C, 63.62; H, 8.14. Found: C, 63.40; H, 8.13.

Extraction constants (CH$_2$Cl$_2$/H$_2$O) were found to be: Na$^+$, 15.7%; K$^+$, 10.2%.

EXAMPLE 7

(4-Propyl-2-methoxyphenoxy)methyl-15-crown-5 Preparation (4-Allyl-2-methoxyphenoxy)methyl-15-crown-5 (5.00 g, 12.5 mmol), ethanol (absolute, 200 mL) and 10% Pd/ C (0.25 g, 0.23 mmol, 2%), were added to a Parr hydrogenation bottle and placed in the shaker of the apparatus. The hydrogen pressure was adjusted to 65 psi, and the bottle was shaken about 12 hours. The mixture was filtered twice through a Buchner funnel containing 2 sheets of filter paper. The ethanol was removed by evaporation in vacuo to yield pure (4-propyl-2-methoxyphenoxy)methyl-15-crown-5, i.e.,

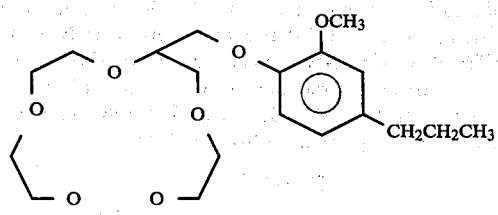

5.00 g, 99% yield, as a colorless to light yellow oil. The extraction constants (CH$_2$Cl$_2$/H$_2$O) were found to be: Na$^+$ 24.3%; K$^+$ 17.6%. The binding constant for sodium cations in 90% methanol solution (log Ks) was found to be 2.94.

General Preparation of Alkoxymethyl or Aryloxymethyl 15-Crown-5 or 16-Crown-5 Molecules (Method 1)

The crown ether compounds whose preparations are described below were prepared by the generalized method below. The method involves the conversion of an aliphatic or aromatic alcohol into a 3-substituted-1,2-propanediol which is then cyclized under the following conditions. The cyclization is carried out in tetrahydrofuran (THF) using 2.1 equivalents of sodium hydride and 1 equivalent of tetraethylene glycol ditosylate or tetraethylene glycol dimesylate. Reactions were stirred mechanically and conducted under an inert atmosphere. The reactions were generally conducted at the reflux temperature of THF. The reactions were conducted for times ranging from 30 min. to 48 hours but were generally near 16 hours. The reactions were then worked up by filtration or addition of water followed by evaporation as seemed appropriate. The crude products were then obtained by dichloromethane extraction followed by the normal washings with water and brine followed by drying over sodium sulfate. Evaporation of the solvent yielded the crown as a crude oil. Pure product was obtained by chomatography over alumina.

The feneral scheme is described by the equation shown below:

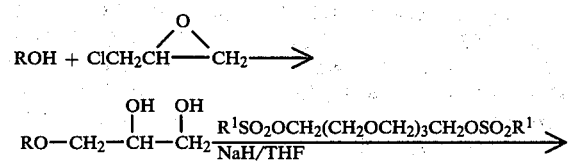

-continued

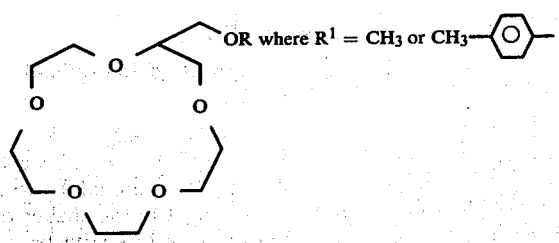

Preparation of Substituted Propanediols from Alcohols (Method 2)

The starting diols for the crown syntheses described below were obtained from epichlorohydrin and either an aliphatic or aromatic alcohol. Slightly different conditions are required for the preparation of RO—CH$_2$—CH(OH)—CH$_2$OH depending on whether R is aliphatic or aromatic, but both cases are described in the report by Juracek, M.; Makes, J.; Ulbrich, V.; Collect, Czech. Chem. Commun., 1964, 29, 1466.

EXAMPLE 8

(2-Methoxyphenoxy)methyl-15-crown-5 Preparation 3-(2-Methoxyphenoxy)-1,2-propanediol was prepared as referenced in Method 2 and obtained as a white solid, melting point 78.5°–80°, in 80% yield.

A 500 mL, 3-necked, round bottomed flask was equipped with 125 mL pressure-equalizing addition funnel, a reflux condenser and a glass stopper. The flask was charged with sodium hydride (5.28 g, 0.11 mol). The NaH was washed (hexanes, 3×100 mL) to remove paraffin oil. THF (200 mL) was added to the flask and the NaH suspended with magnetic stirring. 3-(2-Methoxyphenoxy)-1,2-propanediol (9.90 g, 0.05 mol) and tetraethylene glycol ditosylate (25.1 g, 0.05 mol) were dissolved in THF (75 mL) and added dropwise to the refluxing THF-NaH suspension over approximately 3 hours. The reaction mixture was stirred overnight at reflux. The reaction mixture was allowed to cool and then filtered through a large Buchner funnel. The THF was removed by rotary evaporation and the residue taken up in CH$_2$Cl$_2$ (100 mL). The organic solution was washed with water, brine and then dried over sodium sulfate. The crude product (16.3 g, 92%) was obtained as an amber oil. Chromatography over alumina afforded (2-methoxyphenoxy)methyl-15-crown-5, i.e.,

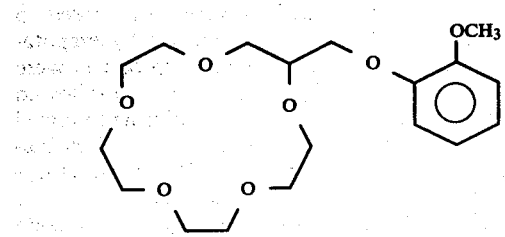

in 70% yield. NMR(CDCl$_3$, delta) 3.6–4.0 (bd, 22H), 4.10 (d, 2H), 6.82 (s, 4H). IR(neat): 3060, 2870, 1593, 1505, 1455, 1355, 1330, 1290, 1255, 1237, 1180, 1120 (s), 980, 940, 870, 845, 762, 740 cm$^{-1}$. Anal. Calcd for C$_{18}$H$_{28}$O$_7$: C, 60.66; H, 7.92. Found: C, 60.48; H, 8.20. Extraction constants (CH$_2$Cl$_2$/H$_2$O) were found to be Na$^+$, 15.7%; K$^+$, 10.2%.

EXAMPLE 9

(4-Methoxyphenoxy)methyl-15-crown Preparation 3-(4-Methoxyphenoxy)-1,2-propanediol was prepared by the method described in Method 2 above in 75% yield (mp: 73°–74° C.). Using the method described in Example 8 above, 3-(4-methoxyphenoxy)-1,2-propanediol (19.8 g, 0.10 mol), NaH(10,56 g, 0.22 mol) and tetraethylene glycol (50.2 g, 0.10 mol) were converted in a total of 550 mL of THF into (4-methoxyphenoxy)methyl-15-crown-5, i.e.,

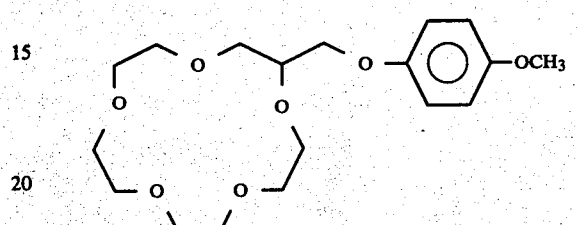

[29% yield after column chromatography (0–10% 2-propanol/hexanes)]. NMR (CDCl$_3$, delta) 3.5–3.9(bd, 21H, 3.9–4.2(bd, 3H), 6.77(s, 4H). IR 3040, 1615, 1590, 1510, 1465, 1350, 1290, 1230, 1175, 1120(s), 1035, 980, 940, 825, 745 cm$^{-1}$. Anal. Calcd for C$_{18}$H$_{28}$O$_7$: C, 60.66; H, 7.92. Found: C, 60.45; H, 8.11. Extraction constants (CH$_2$Cl/H$_2$O) were found to be Na$^+$, 6.4%; K$^+$, 10.7%.

EXAMPLE 10

Phenoxymethyl-15-crown-5 Preparation

3-Phenoxy-1,2-propanediol was prepared as described in Method 2 above in 78% yield, mp 56°–57°. Using the method described in Example 8 above, 3-phenoxy-1,2-propanediol (16.8 g, 0.10 mol), NaH (10.56 g, 0.22 mol) and tetraethylene glycol ditosylate (50.2 g, 0.10 mol) were converted in a total of 550 mL of THF into phenoxymethyl-15-crown-5, i.e.,

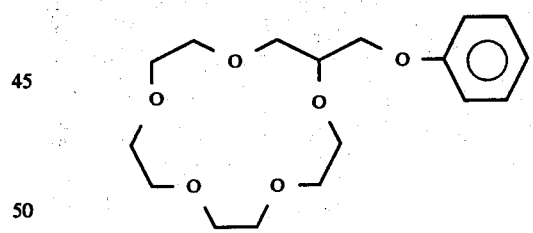

which was obtained as a pale yellow oil in 32% yield after column chromatography (0–10% 2-propanol/hexanes). NMR (CDCl$_3$, delta) 3.70(bs, 19H), 3.78(bd, 2H), 6.5–7.1(m, 5H). IR 3060, 3040, 2870, 1940, 1840, 1770, 1595, 1495, 1455, 1350, 1290, 1245, 1120(s), 1040, 980, 935, 875, 845, 810, 755, 690 cm$^{-1}$. Anal. Calcd for C$_{17}$H$_{26}$O$_6$: C, 62.56; H, 8.03. Found: C, 62.55; H, 8.23. Extraction constant (CH$_2$Cl$_2$/H$_2$O) were found to be Na$^-$, 4.0%; K$^+$, 4.3%.

EXAMPLE 11

[4-(2-Hydroxypropyl)-2-methoxyphenoxy]methyl-15-crown-5 Preparation

A 50 mL, 3-necked flask was equipped with a 10 mL addition funnel, a condenser and a glass stopper. Mercuric acetate (0.96 g, 3.0 mmol), THF (5 mL) and H$_2$O (5 mL) were placed in the flask and stirred with a magnetic stirring bar. (4-Allyl-2-methoxyphenoxy)methyl-15-crown-5 (1.00 g, 2.5 mmol) was added to the reaction flask via pipet. The pipet was rinsed with a little THF and the rinse added to the flask. The reaction mixture was stirred for 1 hour at ambient temperature. The mixture was then made basic by adding 3 M NaOH (5 mL) to the reaction flask. The oxymercurial intermediate was reduced to the alcohol by adding a 1.0 M NaBH$_4$/10% NaOH solution (1.5 mL). The resulting gray mixture was stirred for 0.5 hours until the mercury had coagulated. The solution was then decanted into a separatory funnel. Two phases were obtained after saturation of the aq. phase with NaCl. The phases were separated and the THF was removed by evaporation in vacuo. The residue was taken up in CH$_2$Cl$_2$ (25 mL) and stirred to coagulate any residual mercury. The solution was then decanted, washed with H$_2$O (10 mL) and dried (Na$_2$SO$_4$). The CH$_2$Cl$_2$ was removed by rotary evaporation. The product, i.e.,

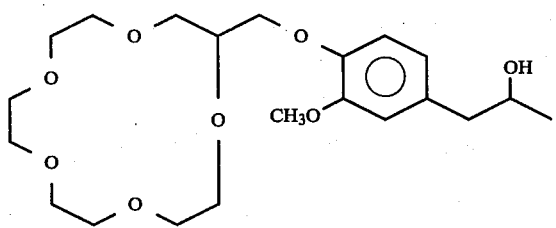

was analyzed by NMR (CDCl$_3$): 1.2 (d, 3H), 2.6 (d, 2H), 3.3-4.2 (m, 26H), 6.7 (m, 3H) and IR (neat): 3450 cm$^{-1}$ (—OH). Extraction constants (CH$_2$Cl$_2$/H$_2$O) were found to be: Na$^+$ 18.7%; K$^+$, 15.1%.

EXAMPLE 12

Methoxymethyl-15-crown-5 Preparation

3-Methoxy-1,2-propanediol was prepared as described in Method 2 above in 78% yield, (bp 115°-119°/20mm). Using the method described in Example 8 above, 3-methoxy-1,2-propanediol (10.6 g, 0.10 mol), NaH (10.56 g, 0.22 mol) and tetraethylene glycol (50.2 g, 0.10 mol) were converted in a total of 550 mL of THF into methoxymethyl-15-crown-5, i.e.,

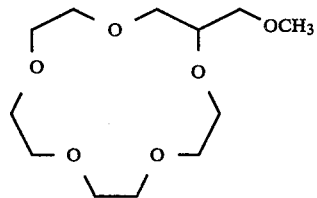

[23% yield of a pale yellow oil after column chromatography (0-4% 2-propanol/pet. ether)]. NMR (CDCl$_3$ delta) 3.46 (s, 3H), 3.76 (bs, 21H); IR 2860, 1445, 1350, 1290, 1250, 1195, 1120(s), 975, 930, 840 cm$^{-1}$; Anal. Calcd for C$_{12}$H$_{24}$O$_6$: C, 54.53; H, 9.15. Found: C, 54.70; H, 9.38. Extraction constants (CH$_2$Cl$_2$/H$_2$O) were found to be: Na$^+$, 5.1%, K$^+$, 3.3%.

EXAMPLE 13 tert-Butoxymethyl-15-crown-5 Preparation 3-t-Butoxy-1,2-propanediol was prepared by the method of Montanari and Tundo (*Tetrahedron Letters,* 1979, 5055) in 6% yield and has properties identical to those reported. NMR (CDCl$_3$, delta) 1.20 (s, 9h9, 2.4-3.0 (bd, 2H), 3.4-3.8 (bt, 5H); IR 3380 (OH). Using the method described above, 3-t-butoxy-1,2-propanediol (14.8g, 0.10 mol), NaH (10.56 g, 0.22 mol) and tetraethylene glycol ditosylate (50.2 g, 0.10 mol) were converted in a total of 550 mL THF into tert-butoxymethyl-15-crown-5, i.e.,

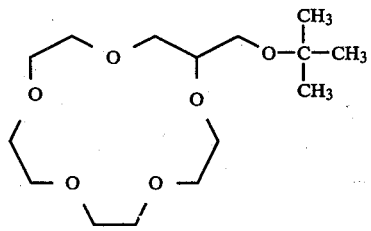

[a colorless oil, 46% yield after column chromatography (0-2% 2-propanol/pet. ether)]. NMR (CDCl$_3$, delta 1.12(s, 9h), 3.73(bs, 21H). IR 2960, 2860, 1615, 1460, 1385, 1360, 1290, 1250, 1190, 1130(s), 980, 935, 875, 840, 750 cm$^{-1}$. Anal. Calcd for C$_{15}$H$_{30}$O$_6$; C, 56.80; H, 9.87. Found: C, 58.70; H, 10.11. Extraction constants (CH$_2$Cl$_2$/H$_2$O) were found to be: Na$^+$, 7.3%; K$^+$, 8.2%.

EXAMPLE 14

(2-Methoxyethoxy)methyl-15-crown-5 Preparation 3-(2-Methoxyethoxy)-1,2-propanediol was prepared as described in Method 2 above from 2-methoxyethanol, in 40% yield, bp 155°-157°/20 mm). Using the method described in Example 8 above, 3-(2-methoxyethoxy)-1,2-propanediol 15 g, 0.10 mol), NaH 810.56 g, 0.22 mol) and tetraethylene glycol (50.2 g, 0.10 mol) were converted in a total of 550 mL of THF into (2-methoxyethoxy)methyl-15-crown-5, i.e.,

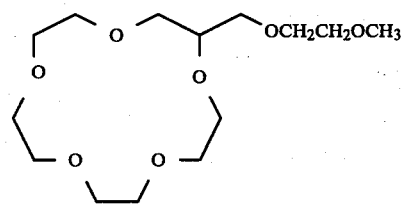

[a pale yellow oil, 65% yield after column chromatography (0-5% 2 propanol/pet. ether)]. NMR (CDCl$_3$, delta) 3.46 (s, 3H), 3.5-3.9(bd, 25H). IR 2880, 1505, 1450, 1355, 1290, 1250, 1195, 1120(s), 1030, 980, 935, 870, 845 cm$^{-1}$. Anal. Calcd for C$_{14}$H$_{28}$O$_7$: C, 54.53; H, 9.15. Found: C, 54.54; H, 9.28 Extraction constants (CH$_2$Cl$_2$/H$_2$O) were found to be: Na$^+$, 18.0%; K$^+$, 13.7%.

EXAMPLE 15

(2-Butoxyethoxy)methyl-15-crown-5 Preparation 3-(2-Butoxyethoxy)-1,2-propanediol was prepared by Method 2 noted above in 83% yield. Using the method described in Example 8 above, 3-(2-butoxyethoxy)-1,2-propanediol (19.2 g, 0.10 mol), NaH (10.56 g, 0.22 mol), and tetraethylene glycol ditosylate (50.2 g, 0.22 mol) were converted in a total of 550 mL of THF into (2-butoxyethoxy)methyl-15-crown-5, i.e.,

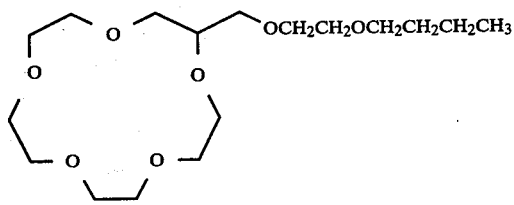

[a pale yellow oil, 55% yield after column chromatography (0–2% 2-propanol/pet. ether)]. NMR (CDCl₃, delta) 0.93(bt, 3H), 1.3–1.7(m, 4H), 3.4–3.9(bd, 27H). IR 2860, 1450, 1350, 1290, 1250, 1120(s), 1040, 980, 935, 840 Cm⁻¹. Anal. Calcd for $C_{17}H_{34}O_7$: C, 58.25; H, 9.78. Found: C, 58.40; H, 10.07. Extraction constants ($CH_2Cl_2/H_2$) were found to be: Na⁺, 11.2%; k⁺, 10.9%.

EXAMPLE 16

[2-(2-Methoxyethoxy)ethoxy]methyl-15-crown-5 Preparation

3-[2-(2-Methoxyethoxy)ethoxy]-1,2-propanediol was prepared from 2-(2-methoxyethoxy)ethanol by the Method 2 noted above in 73% yield, bp 110–118/0.05 mm). Using the method in Example 8 described above, 3-[2-(2-methoxyethoxy)ethoxy]-1,2-propanediol (19.4 g, 0.10 mol), NaH (10.56 g, 0.22 mol) and tetraethylene glycol ditosylate (50.2 g, 0.10 mol) were converted in a total of 550 mL of THF into [2-(2-methoxyethoxy)ethoxy]methyl-15-crown-5, i.e.,

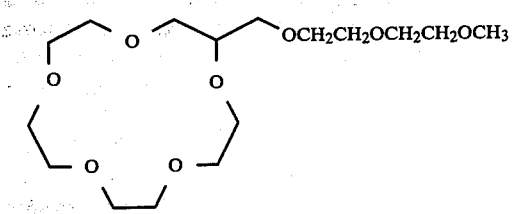

[a pale yellow oil, 48% yield after column chromatography (0–4% 2-propanol/pet. ether]. NMR (CDCl₃, delta) 3.33(s, 3H), 3.70(bs, 29H). IR 2860, 1900, 1615, 1450, 1350, 1290, 1245, 1195, 1120(s), 1040, 980, 935, 870, 840 cm⁻¹. Anal Calcd for $C_{16}H_{32}O_8$: C, 54.53; H, 9.15. Found: C, 54.40; H, 9.42. Extraction constants ($CH_2Cl_2/H_2O$) were found to be Na⁺, 15.7%; K⁺, 24.4%.

Alkylation of Hydroxymethyl-15-crown-5: General Procedure for the Preparation of Alkoxymethyl-15-crowns-5

(Method 3)

A 10 mL flask fitted with a magnetic stirrer and a condenser was charged with hydroxymethyl-15-crown-5 whose preparation is described above (0.62 g, 0.025 mol), the appropriate alkylating agent (0.025 mol), 50% aqueous sodium hydroxide (2.0 g) and dichloromethane (1.0 mL). This mixture was stirred overnight at 25° C. under a nitrogen atmosphere. Dichloromethane (25 mL) was added and the organic phase was washed with ice water (3×20 mL), dried, filtered and evaporated at reduced pressure to yield the analytically pure ether unless otherwise specified.

EXAMPLE 17

Butoxymethyl-15-crown-5 Preparation

The title compound was prepared by Method 3 described above using 0.69 g (5 mmol) of n-butyl bromide. The product was isolated (0.50 g, 64%) as a light yellow oil, i.e.,

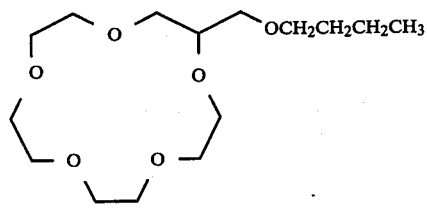

NMR (CDCl₃, delta) 0.7–1.9 (bm, 7H), 3.53 (bs, 23H); IR 2950–2850 (s), 1450, 1350, 1290, 1240, 1120 (s), 980, 940, 840 cm⁻¹. Anal. Calcd. for $C_{15}H_{30}O_6$: C, 58.80; H, 9.87. Found: C, 58.70; H, 10.11.

EXAMPLE 18

2-[2-(2-Hydroxyethoxy)ethoxy]ethoxymethyl-15-crown-5

A 50 mL, three-necked, round-bottomed flask was equipped with a magnetic stirbar, reflux condenser, 10 mL addition funnel and a glass stopper. The flask was charged with NaH (0.24 g, 0.005 mol) which was immediately covered with THF (10 mL). Hydroxymethyl-15-crown-5 was dissolved in THF (5 mL) and added dropwise to the reaction mixture. The mixture was stirred for 20 minutes and became brown. PhCH₂(OCH₂CH₂)₃OTs in THF (5 mL) was added dropwise. The mixture was stirred for an additional 2 hours, filtered and the solvent evaporated in vacuo. The crude product was partitioned between water and dichloromethane and then the solvent was evaporated. The crude amber oil (2.1 g, 89%) was chromatographed (alumina) to afford 2-[2-(2-benzyloxyethoxy)ethoxy]ethoxymethyl-15-crown-5, i.e.,

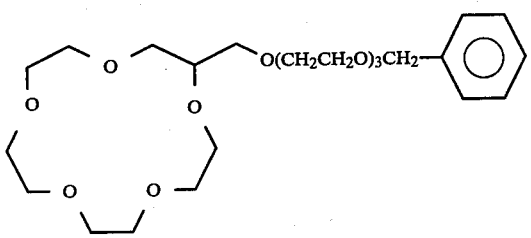

as a light yellow oil. The oil described above (4.0 g from several preparations) was placed in a Parr hydrogenation bottle with ethanol (75 mL) and 0.5 g of 10% Pd on C catalyst. Hydrogen was introduced (to 60 psi) and the mixture was shaken at ambient temperature for 24 hours and then filtered. The solvent was evaporated to afford 2-[2-(2-hydroxyethoxy)ethoxy]ethoxymethyl-15-crown-5, i.e.,

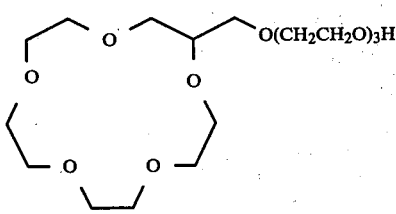

as a nearly colorless oil in 94% yield. NMR$\delta$ 2.83 (broad t, 1H, —OH), 3.69 (m, 33H). IR 3300 (OH), 2850, 1450, 1350, 1290, 1245, 1110, 1030, 930, 845. Anal. calcd. for $C_{17}H_{34}O_9$: C, 53.39; H, 8.96. Found: C, 53.36; H, 9.20. Extraction constants: $Na^+$, 15.3; $K^+$, 26.5.

EXAMPLE 19

2-[2-(2-Methoxyethoxy)ethoxy]ethoxymethyl-15-crown-5

A 50 mL, 3-necked, round-bottomed flask was equipped with a 10 mL addition funnel, a reflux condenser and a nitrogen inlet. The flask was then charged with NaH (0.13 g) and washed three times with 5 mL portions of hexane. THF (15 mL) was added and then a solution of the compound of Example 18, i.e., 2-[2-(hydroxyethoxy)ethoxy]ethoxymethyl-15-crown-5, (1.00 g) in THF (5 mL), was added and the resulting solution stirred for 20 minutes. Dimethyl sulfate (0.33 g) was then added in one portion and the mixture allowed to stir for 1 hour, after which time it was filtered and the solvent evaporated. Chromatography of the crude amber oil (1.00 g 97%) over alumina (20 g) afforded 2-[2-(2-methoxyethoxy)ethoxy]ethoxy-methyl-15-crown-5, i.e.,

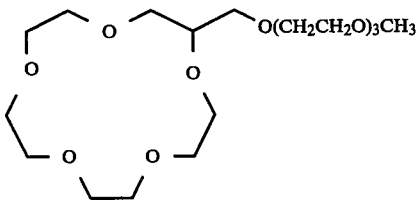

as a colorless oil (0.72 g, 70%). NMR$\delta$ 3.37 (s, 3H), 3.68 (m, 33H). IR 2860, 1445, 1350, 1290, 1245, 1195, 1120 (S), 1030, 980, 940, 845, 725. Anal. calcd. for $C_{18}H_{36}O_9$: C, 54.53; H, 9.15. Found: C, 54.25; H, 9.40. Extraction constants: $Na^+$, 19.8; $K^+$, 32.1.

EXAMPLE 20

(1-Naphthyloxy)methyl-15-crown-5

A 1 L, three-necked, round-bottomed flask was equipped with a mechanical stirrer, a 125 mL addition funnel, a reflux condenser, with nitrogen inlet atop. The flask was charged with NaH (5.04 g) which was washed three times with hexanes (100 mL portions) to remove the mineral oil. THF (200 mL) was then added with vigorous stirring. The suspension was heated to reflux. 1,2-Dihydroxy-3-(1-naphthyloxy)propane (prepared according to the procedure of Ulbrich et al, *Coll. Czech. Chem. Commun.* 1964, 29, 1466) (10.9 g) and tetraethylene glycol ditosylate (25.1 g) in THF solution (75 mL) were added dropwise to the mixture over a 1.5 hour period. Reflux was continued for ca. 16 hours, cooled and then filtered. The solvent was evaporated and the residue dissolved in dichloromethane. The latter was washed with water, brine and then dried over sodium sulfate. Evaporation of the dichloromethane left a crude, brown oil (16.4 g, 87%) which was chromatographed over 300 g of alumina to yield (1-naphthyloxy)-methyl-15-crown-5, i.e.,

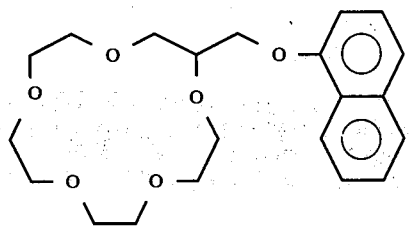

as a pale yellow oil in 7.5% yield. NMR$\delta$ 3.6–4.2 (m, 21H), 6.8 (m, 1H), 7.4 (m, 4H), 7.8 (m, 1H), 8.2 (m, 1H). IR 3050, 2860, 1720, 1630, 1600, 1580, 1510, 1460, 1400, 1355, 1270, 1245, 1180, 1130 (S), 1100, 1020, 985, 935, 845, 795, 775, 740, 660; Anal. calcd. for $C_{21}H_{28}O_6$: C, 67.00; H, 7.50. Found, C, 66.97; H, 7.71.

EXAMPLE 21

(8-Quinolinyloxy)methyl-15-crown-5 Preparation

3-Quinolinyloxy-1,2-propanediol was prepared from 8-hydroxyquinoline as described in Method 2 above.

A 500 mL, 3-necked, round-bottomed flask was equipped with a mechanical stirrer, a reflux condenser and a Claisen head. The Claisen head was coupled to a 100 mL round-bottomed flask with a length of flexible rubber hose. This flask and hose assembly was used to introduce solids to the reaction flask. The Claisen head also served as the $N_2$ inlet, and the nitrogen was vented through the reflux condenser. The flask was purged with a vigorous stream of nitrogen for 10 minutes prior to use. Dimethylformamide (DMF 200 mL, freshly distilled from CaO) was then added to the reaction flask. The NaH (5.04 g, 0.105 mol) was added in several small portions from the 100 mL round-bottomed flask. The DMF/NaH suspension was heated to ca. 60°. The 3-quinolinyloxy-1,2-propanediol (10.95 g, 0.05 mol) was then added to the reaction flask in the same way as the NaH. The reaction mixture was stirred for 15 minutes. The tetraethylene glycol ditosylate was dissolved in DMF (50 mL) and was placed in a 125 mL addition funnel. The addition funnel then replaced the flexible hose and 100 mL round-bottomed flask. The ditosylate was then added to the reaction flask in a stream, and the reaction mixture was stirred for 16 hours at ca. 60°. It was then allowed to cool, and the salts were removed by filtration through a large Buchner funnel. Most of the DMF was removed by evaporation in vacuo. The residue was taken up in $CH_2Cl_2$ (200 mL). This solution was washed with $H_2O$ (50 mL), brine (50 mL) and dried ($Na_2SO_4$). The $CH_2Cl_2$ was removed by rotary evaporation. This crude, reddish brown product was column chromatographed over alumina (eluent: 0–4% 2-propanol/petroleum ether, v/v) to yield 8-quinolinyloxymethyl-15-crown-5, i.e.,

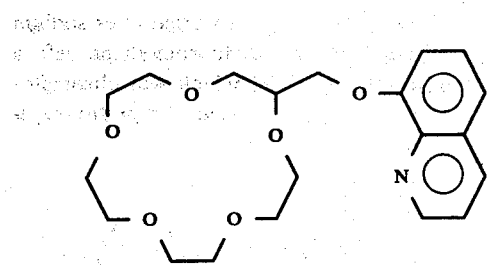

(10.69 g, 57% as a pale, yellow oil. NMR (CDCl$_3$, delta): 3.6–4.6 (m, 21H); 7.1–7.6 (m, 4H); 8.2 (q, 1H), 9.0 (q, 1H). IR(neat): 3060, 3040, 2860, 1950, 1615, 1595, 1570, 1500, 1470, 1425, 1380, 1360, 1320, 1260, 1185, 1100(s), 990, 940, 875, 845, 820, 790, 750, 730, 705, 640 cm$^{-1}$. Anal. Calcd. for C$_{20}$H$_{27}$NO$_6$: C, 63.65; H, 7.21; N, 3.71. Found: C, 63.60; H, 7.50; N, 3.50. The binding constant (log Ks) in 90% (by weight) methanol was found to be 3.39 (Na+).

I claim:
1. (4-allyl-2-methoxyphenoxy)methyl-15-crown-5.
2. (4-propyl-2-methoxyphenoxy)methyl-15-crown-5.
3. [4-(2-hydroxypropyl)-2-methoxyphenoxy]methyl-15-crown-5.
4. (8-quinolinyloxy)methyl-15-crown-5.
5. (2-methoxyphenoxy)methyl-15-crown-5.
6. 2-[2-(2-benzyloxyethoxy)ethoxy]ethoxymethyl-15-crown-5.